United States Patent
Tang et al.

(10) Patent No.: US 8,518,946 B2
(45) Date of Patent: Aug. 27, 2013

(54) SALTS OF (R)-7-[3-AMINO-4-(2,4,5-TRIFLUOROPHENYL)BUTANOYL]-3-TRIFLUOROMETHYL-5,6,7,8-TETRAHYDROIMIDAZO[1,5-A] PYRAZINE-1-CARBOXYLIC ACID, PREPARATION METHOD AND MEDICAL USE THEREOF

(75) Inventors: Peng Cho Tang, Shanghai (CN);
Piaoyang Sun, Shanghai (CN);
Fanglong Yang, Shanghai (CN);
Jindong Liang, Shanghai (CN);
Guangyuan Shen, Shanghai (CN); Yang Wang, Shanghai (CN); Jiang Fan, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/225,050

(22) Filed: Sep. 2, 2011

(65) Prior Publication Data

US 2012/0065209 A1  Mar. 15, 2012

Related U.S. Application Data

(63) Continuation of application No. PCT/CN2010/000257, filed on Mar. 3, 2010.

(30) Foreign Application Priority Data

Mar. 5, 2009  (CN) .......................... 2009 1 0047075

(51) Int. Cl.
*A61K 31/495*  (2006.01)
(52) U.S. Cl.
USPC ......................................... 514/249; 544/350
(58) Field of Classification Search
USPC ......................................... 514/249; 544/350
See application file for complete search history.

(56) References Cited

U.S. PATENT DOCUMENTS 6,110,949 A  8/2000  Villhauer

FOREIGN PATENT DOCUMENTS

| CA | 2706735 | * | 7/2009 |
| CN | 1524082 A | | 8/2004 |
| CN | 101468988 A | | 7/2009 |
| WO | 98/19998 | | 5/1998 |
| WO | 2009/082881 | | 7/2009 |

OTHER PUBLICATIONS

International Search Report for PCT/CN2010/00257, mailed Jun. 3, 2010.
Lene Hansen et al., "Glucagon-Like Peptide-1-(7-36)Amide Is Transformed to Glucagon-Like Peptide-1-(9-36)Amide by Dipeptidyl Peptidase IV in the Capillaries Supplying the L Cells of the Porcine Intestine", Endocrinology 1999, vol. 40, No. 11, pp. 5356-5363.

* cited by examiner

*Primary Examiner* — Douglas M Willis
(74) *Attorney, Agent, or Firm* — Staas & Halsey LLP

(57) ABSTRACT

Pharmaceutically acceptable salts of (R)-7-[3-amino-4-(2,4,5-trifluorophenyl)-butyryl]-3-trifluoromethyl-5,6,7,8-tetrahydro-imidazo[1,5-a]pyrazine-1-formic acid, their preparation methods, compositions containing the said pharmaceutical salts and their use as medicaments, especially as dipeptidyl peptidase IV (DPP-IV) inhibitors are disclosed. Of the many acceptable salts, one example is the following.

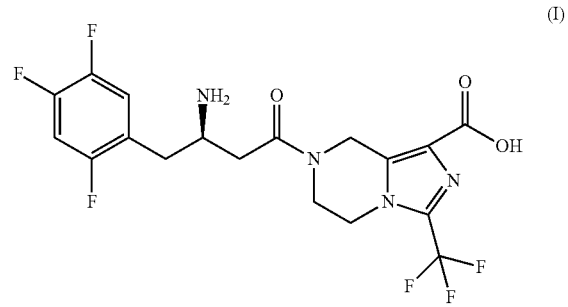

(I)

5 Claims, No Drawings

SALTS OF (R)-7-[3-AMINO-4-(2,4,5-TRIFLUOROPHENYL)BUTANOYL]-3-TRIFLUOROMETHYL-5,6,7,8-TETRAHYDROIMIDAZO[1,5-A]PYRAZINE-1-CARBOXYLIC ACID, PREPARATION METHOD AND MEDICAL USE THEREOF

CROSS REFERENCE TO RELATED APPLICATION

This application is a continuation application filed under 35 U.S.C. §111(a), claiming the benefit under 35 U.S.C. §120 and §365(c) of a PCT International Application Number PCT/CN2010/000257, filed Mar. 3, 2010, it being further noted that foreign priority benefit is based upon Chinese Patent Application 200910047075.4, filed Mar. 5, 2009 in the State Intellectual Property Office of P.R. China, the disclosures of which are thereby incorporated by reference.

FIELD OF THE INVENTION

The present invention relates to pharmaceutically acceptable salts of (R)-7-[3-amino-4-(2,4,5-trifluorophenyl)-butanoyl]-3-trifluoromethyl-5,6,7,8-tetrahydro-imidazo[1,5-a]pyrazine-1-carboxylic acid, methods for their preparation, pharmaceutical compositions containing them and their use as therapeutical agent, particularly their use as a dipeptidyl peptidase IV (DPP-IV) inhibitor.

BACKGROUND OF THE INVENTION

Diabetes was recorded long before. It is a metabolic disease characterized by chronic hyperglycemia because of absolute or relative lack of insulin in the human body resulting in increased concentrations of glucose in the blood and dramatic glucose discharges in urine, along with sugar, lipid and protein metabolic disorder and physiologically expresses increased drinking, increased urining, increased eating, weight loss, dizziness, weakness and other symptoms.

Persistent or uncontrolled hyperglycemia is associated with increased morbidity and mortality. Often abnormal glucose homeostasis is associated directly or indirectly with alterations of the lipid, lipoprotein and apolipoprotein metabolism and other metabolic and hemodynamic diseases. Patients with type 2 diabetes mellitus are at especially increased risk of macrovascular and microvascular complications, such as coronary heart disease, stroke, peripheral vascular disease, hypertension, nephropathy, neuropathy, and retinopathy etc. Therefore, therapeutical control of glucose homeostasis, lipid metabolism, hypertension and the like is very important for the clinical treatment of diabetes mellitus.

There are two generally recognized forms of diabetes. In type 1 diabetes, i.e., insulin-dependent diabetes mellitus (IDDM), patients produce little or no insulin which is the hormone that regulates glucose utilization. In type 2 diabetes, i.e., noninsulin-dependent diabetes mellitus (NIDDM), patients often have plasma insulin levels that are the same or even elevated compared to nondiabetic subjects. However, these patients have developed a resistance to the insulin which has stimulating effect on glucose and lipid metabolism in the main insulin-sensitive tissues such as muscle, liver and 25 adipose tissues, and the plasma insulin levels, even if elevated, are insufficient to overcome the pronounced insulin resistance.

Insulin resistance is not primarily due to a diminished number of insulin receptors but also to a post-insulin receptor binding defect that is not yet understood so far. This resistance to insulin responsiveness results in insufficient insulin-dependent activation of glucose uptake, oxidation and storage in muscle, and inadequate repression of lipolysis in adipose tissue and regulation of glucose production and secretion in the liver.

Dipeptidyl peptidase-IV (DPP-IV) is a serine protease which cleaves N-terminal dipeptides from a polypeptide containing a proline residue at the penultimate position. Although the biological role of DPP-IV in mammalian systems has not been completely established, it is believed to play an important role in neuropeptide metabolism, T-cell activation, adhesion and invasion of cancer cells to the endothelium and the entry of HIV into lymphoid cells (WO98/19998).

Recently, it is discovered that DPP-IV is responsible for preventing glucagon-like peptide-1 (GLP-1) secretion. More particularly, DPP-IV cleaves the N-terminal His-Ala dipeptide of GLP-1, thus degrading the active GLP-1(7-36)$NH_2$ to the inactive GLP-1(9-36)$NH_2$ (Endocrinology, 1999, 140: 5356-5363). Under physiological conditions, the half-life of the whole GLP-1 in blood circulation is short. The inactive metabolite of GLP-1 after degradation by DPP-IV can bind with GLP-1 receptors, thus antagonize active GLP-1, and shorten the physiological responses to GLP-1. However, DPP-IV inhibitors can protect endogenous or even exogenous GLP-1 from being inactivated, and thus significantly increase GLP-1 bioactivity (5- to 10-fold). Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM) (U.S. Pat. No. 6,110,949).

Although some DPP-IV inhibitors have been disclosed, there is no long effective drug at present. Improved DPP-IV inhibitors are still needed.

The purpose of the present invention is to provide a series of compounds which have DPP-IV inhibition activity and can be used for the treatment of diabetes or similar disease, or used as palliative drugs.

The application PCT/CN2008/001936 submitted by the applicant of the present invention on 4 Jan. 2009 described a novel tetrahydro-imidazo[1,5-a]pyrazine derivatives and their uses as DPP-IV inhibitor. The example 10 disclosed in it was (R)-7-[3-amino-4-(2,4,5-trifluoro-phenyl)-butanoyl]-3-trifluoromethyl-5,6,7,8-tetrahydro-imidazo[1,5-a]pyrazine-1-carboxylic acid hydrochloride which was confirmed to have an excellent inhibition activity against DPP-IV according to the test. Therefore this application was whole incorporated here as reference.

The other purpose of the present invention is to provide the pharmaceutically acceptable salts of compounds represented by formula (I) and their compositions to improve their solubility, bioavailability, hypoglycemic activity and pharmacokinetics.

SUMMARY OF THE INVENTION

The present invention is directed to provide novel pharmaceutically acceptable salts of (R)-7-[3-amino-4-(2,4,5-trifluorophenyl)butanoyl]-3-trifluoromethyl-5,6,7,8-tetrahydro-imidazo[1,5-a]pyrazine-1-carboxylic acid, methods for their preparation, pharmaceutical compositions containing them and their use as therapeutical agent, particularly their use as dipeptidyl peptidase IV inhibitor. The salts of the compound represented by formula (I) have excellent activity in the treatment of diabetes, improved solubility, good activity and bioavailability in vivo, as well as lower toxicity, which were good candidates in the preparation of a medicament for the treatment of diabetes.

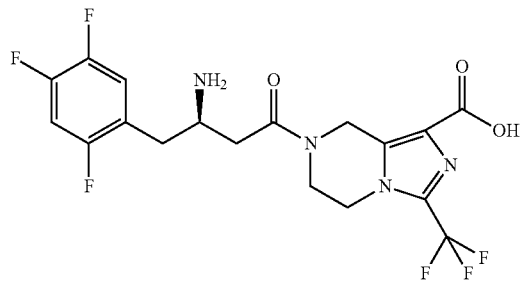

(I)

The present invention provides pharmaceutical acceptable salts of the compounds of formula (I). The term "pharmaceutical acceptable salts" refers to pharmaceutical nontoxic acid addition salts or base addition salts. The acid addition salts are those formed from the compounds of formula (I) and organic or inorganic acids, including hydrochloride, phosphate, hydrophosphate, sulfate, bisulfate, sulfite, acetate, oxalate, malonate, pentanoate, glutamate, oleate, palmitate, stearate, laurate, borate, p-toluenesulfonate, methanesulfonate, malate, tartrate, benzoate, pamoate, salicylate, vanillate, mandelate, succinate, gluconate, lactobionate, and lauryl sulfonate, preferably phosphate. The base addition salts are those formed from the compounds of formula (I) and organic or inorganic base, including those formed with such as alkali metals, amine or quaternary ammonium, such as sodium salt, lithium salt, potassium salt, calcium salt, magnesium salt, amine salt, tetramethyl quaternary ammonium salt, tetraethyl quaternary ammonium salt, choline salt, preferably choline salt. The amine salts are those formed from the compounds of formula (I) and amine including ammonia, primary amine, secondary amine and tertiary amine, such as methylamine salt, dimethylamine salt, trimethylamine salt, triethylamine salt, ethylamine salt, ethanolamine salt, lysine salt and arginine salt, preferably ethanolamine salt.

Representative pharmaceutically acceptable salts of the compounds of formula (I) of the present invention include, but are not limited to:

| Example No. | Structure | Name |
|---|---|---|
| 1 | 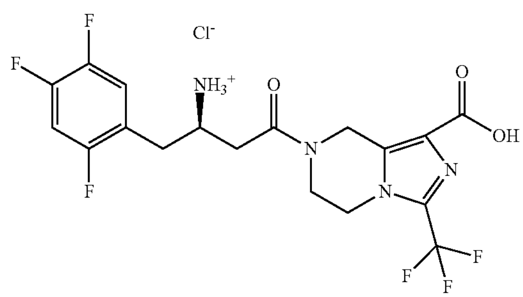 [SMILES: [NH3+][C@@H](CC(=O)N1CCn2c(C(F)(F)F)nc(C(=O)O)c2C1)Cc1cc(F)c(F)cc1F ; [Cl-]] | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid hydrochloride |
| 2 | 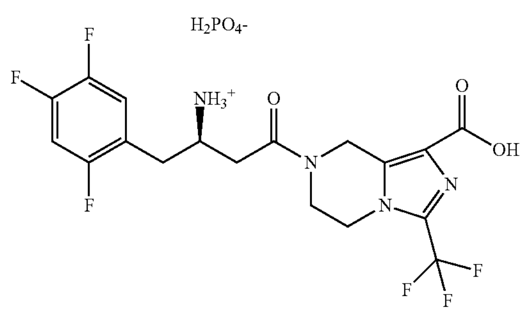 [SMILES: [NH3+][C@@H](CC(=O)N1CCn2c(C(F)(F)F)nc(C(=O)O)c2C1)Cc1cc(F)c(F)cc1F ; "H2PO4-"] | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid phosphate |
| 3 | 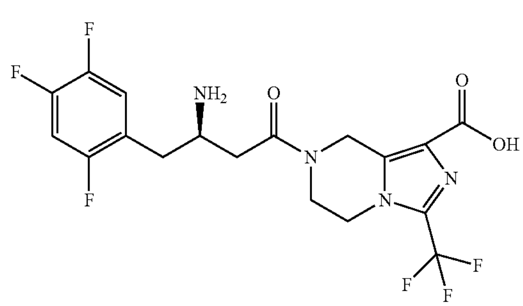 [SMILES: N[C@@H](CC(=O)N1CCn2c(C(F)(F)F)nc(C(=O)O)c2C1)Cc1cc(F)c(F)cc1F] | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid |

-continued

| Example No. | Structure | Name |
|---|---|---|
| 4 | 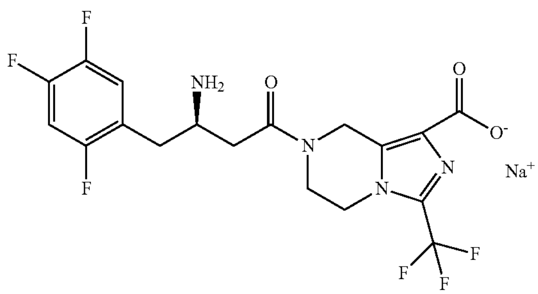 [SMILES: N[C@@H](CC(=O)N1CCn2c(C(F)(F)F)nc(C(=O)[O-])c2C1)Cc1cc(F)c(F)cc1F ; [Na+]] | Sodium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 5 | 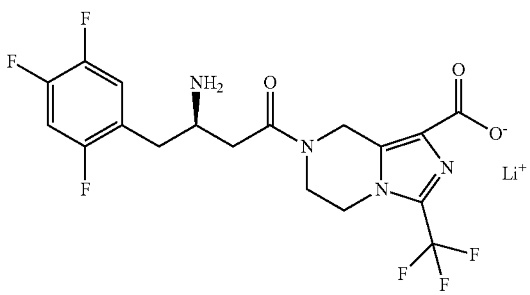 [SMILES: N[C@@H](CC(=O)N1CCn2c(C(F)(F)F)nc(C(=O)[O-])c2C1)Cc1cc(F)c(F)cc1F ; [Li+]] | Lithium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 6 | 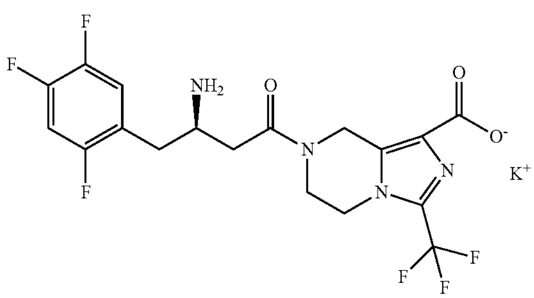 [SMILES: N[C@@H](CC(=O)N1CCn2c(C(F)(F)F)nc(C(=O)[O-])c2C1)Cc1cc(F)c(F)cc1F ; [K+]] | Potassium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 7 | 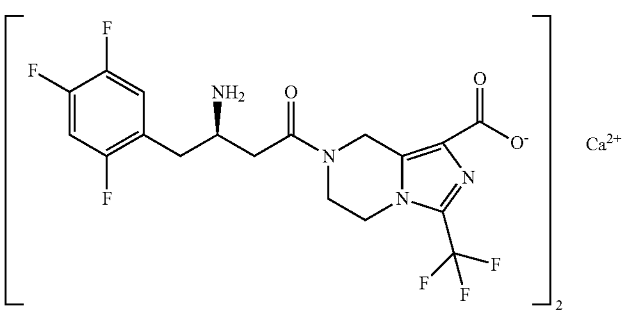 | Calcium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 8 | 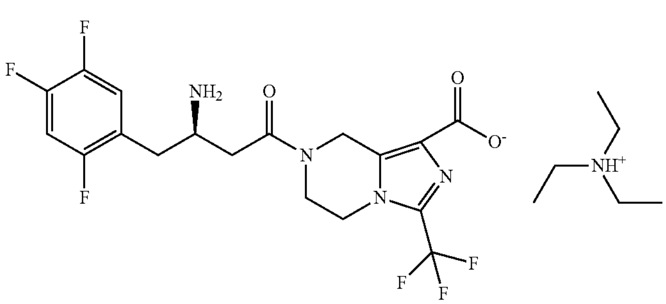 | triethylammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate |

-continued

| Example No. | Structure | Name |
|---|---|---|
| 9 | 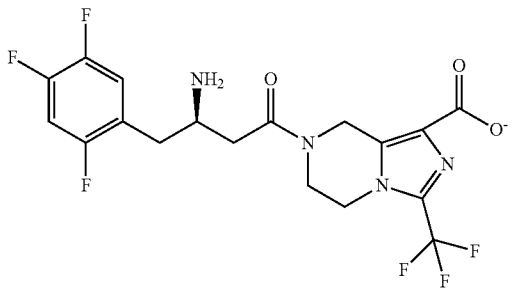 | 2-hydroxyethylammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 10 | 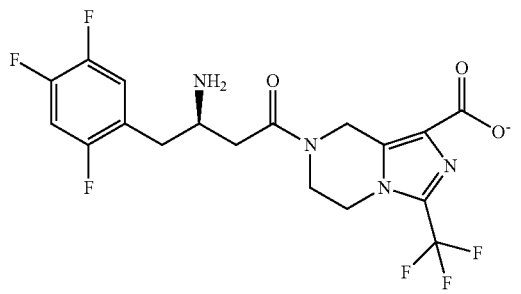 | 2-hydroxyethyl(trimethyl)ammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate |
| 11 | 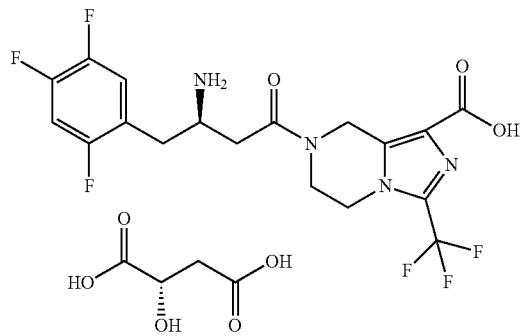 | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S)-2-hydroxybutanedioic acid |
| 12 | 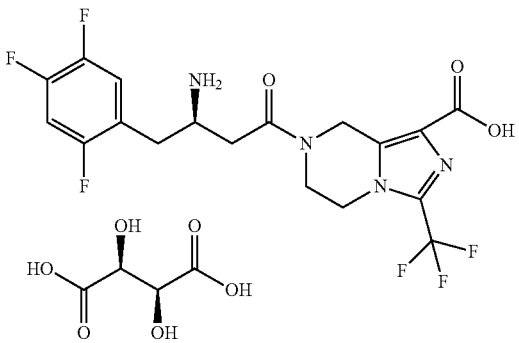 | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S,3S)-2,3-dihydroxybutanedioic acid |

-continued

| Example No. | Structure | Name |
|---|---|---|
| 13 | 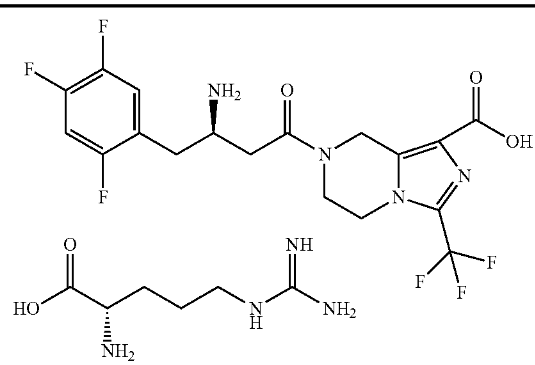 | (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S)-2-amino-5-guanidino-pentanoic acid |

The above salt formation reactions are generally prepared in the conditions of cooling, room temperature or heating. However, it is notable that the reaction temperature has some influence on different salt formation reactions, which is well known by the person skilled in the art. The salt formation reaction temperatures of the present invention ranges from room temperature to the boiling point of the reaction solvent, preferably 0~40° C. The person skilled in the art can easily determine the most prefer reaction temperature of salt formation reaction via conventional techniques.

The present invention relates to the preparation process of the pharmaceutical acceptable salts of compound of formula (I), wherein the process comprises acid addition and base addition to form the salts. The preparation process of acid addition salts comprises following steps of reacting (R)-7-[3-amino-4-(2,4,5-trifluorophenyl)butanoyl]-3-trifluoro-methyl-5,6,7,8-tetrahydro-imidazo[1,5-a]pyrazine-1-carboxylic acid hydrochloride with an alkaline solution and reacting the resulting (R)-7-[3-amino-4-(2,4,5-trifluorophenyl)butanoyl]-3-(trifluoromethyl)-5,6,7,8-tetrahydro-imidazo[1,5-a]pyrazine-1-carboxylic acid with an organic or inorganic acid, wherein the organic or inorganic acid is selected from the group consisting of hydrochloric acid, phosphoric acid, sulfuric acid, sulphurous acid, acetic acid, oxalic acid, malonic acid, pentanoic acid, glutamic acid, oleic acid, palmitic acid, stearic acid, lauric acid, boracic acid, p-toluenesulfonic acid, methanesulfonic acid, malic acid, tartaric acid, benzoic acid, pamoic acid, salicylic acid, vanillic acid, mandelic acid, succinic acid, gluconic acid, lactobionic acid, and lauryl sulfonic acid. The preparation process of base addition salts comprises reacting (R)-7-[3-amino-4-(2,4,5-trifluorophenyl)butanoyl]-3-trifluoromethyl-5,6,7,8-tetrahydro-imidazo[1,5-a]pyrazine-1-carboxylic acid with alkaline metal hydroxide, substituted amine or quaternary ammonium, wherein the alkaline metal hydroxide is selected from sodium hydroxide, lithium hydroxide, potassium hydroxide, calcium hydroxide, magnesium hydroxide, and the amine or the quaternary ammonium is selected from the group consisting of tetramethyl quaternary ammonium, tetraethyl quaternary ammonium, ethanolamine, choline, lysine, arginine, methanamine, dimethylamine, trimethylamine, triethylamine and ethylamine.

The present invention relates to the use of the pharmaceutically acceptable salts of the compounds of formula (I) in the preparation of a medicament for the treatment of type 2 diabetes, hyperglycemia, obesity or insulin resistance.

The present invention relates to the use of the pharmaceutically acceptable salts of the compounds of formula (I) in the preparation of dipeptidyl peptidase (DPP-IV) inhibitor.

The present invention relates to a method for the treatment of type 2 diabetes, hyperglycemia, obesity or insulin resistance, wherein the method comprises administration of therapeutically effective amount of the pharmaceutically acceptable salts of the compounds of formula (I) to the subject.

The present invention relates to a method of inhibiting a dipeptidyl peptidase IV catalytic activity, wherein the method comprises contacting the dipeptidyl peptidase IV with the pharmaceutically acceptable salts of the compounds of formula (I).

The present invention relates to the use of the pharmaceutically acceptable salts of the compounds of formula (I) as a drug in the treatment of type 2 diabetes, hyperglycemia, obesity or insulin resistance.

The present invention relates to the use of the pharmaceutically acceptable salts of the compounds of formula (I) as a drug inhibiting the dipeptidyl peptidase IV (DPP-IV).

The present invention relates to a pharmaceutical composition which comprises therapeutically effective amount of a pharmaceutically acceptable salt of the compounds of formula (I) and a pharmaceutically acceptable carrier. The present invention also relates to the use of the composition in the preparation of a medicament for the treatment of type 2 diabetes, hyperglycemia, obesity or insulin resistance.

The present invention relates to a method for the treatment of type 2 diabetes, hyperglycemia, obesity or insulin resistance, wherein the method comprises administration of therapeutically effective amount of the pharmaceutical composition containing pharmaceutically acceptable salts of the compounds of formula (I) to the subject.

The present invention relates to the use of the pharmaceutical composition containing pharmaceutical salts of the compounds of formula (I) as a drug in the treatment of type 2 diabetes, hyperglycemia, obesity or insulin resistance.

Unless otherwise stated, the following terms used in the specification and claims have the meanings described below.

The term "pharmaceutical composition" refers to a mixture of one or more of the pharmaceutically acceptable salts of the compound described herein or prodrugs thereof with other chemical components such as physiologically/pharmaceutically acceptable carriers. The purpose of the pharmaceutical composition is to facilitate administration of a compound to an organism.

In order to achieve the objectives of the invention, the invention applies the following technical solutions:

The synthesis method of the compound of formula (I) refers to the preparation method described in example 10 of the application PCT/CN2008/001936 submitted by the applicant on Nov. 27, 2008. Thus the disclosure was whole incorporated here as reference.

The method of acid or base addition salt reaction of the compound (R)-7-[3-amino-4-(2,4,5-trifluorophenyl)butanoyl]-3-trifluoromethyl-5,6,7,8-tetrahydro-imidazo[1,5-a]pyrazine-1-carboxylic acid comprises:

The method of acid addition salt reaction comprising reacting (R)-7-[3-amino-4-(2,4,5-trifluorophenyl)butanoyl]-3-(trifluoromethyl)-5,6,7,8-tetrahydroimidazo[1,5-a]pyrazine-1-carboxylic acid hydrochloride with a alkaline solution and reacting the resulting (R)-7-[3-amino-4-(2,4,5-trifluorophenyl)butanoyl]-3-(trifluoromethyl)-5,6,7,8-tetrahydro-imidazo[1,5-a]pyrazine-1-carboxylic acid with an organic or inorganic acid;

The method of base addition salt reaction comprising reacting (R)-7-[3-amino-4-(2,4,5-trifluorophenyl)butanoyl]-3-(trifluoromethyl)-5,6,7,8-tetrahydro-imidazo[1,5-a]pyrazine-1-carboxylic acid with an organic or inorganic base such as alkaline metal hydroxide, substituted amine or quaternary ammonium in organic solvent soluble with water.

DETAILED DESCRIPTION OF THE INVENTION

The following examples are provided to further illustrate the invention, but they should not be considered as the limit of the invention.

The structure of the compounds was confirmed by nuclear magnetic resonance spectroscopy ($^1$HNMR) or mass spectrometry (MS). $^1$H NMR shifts (δ) were given in ppm. $^1$H NMR was determined by a Bruker AVANCE-400 equipment. The solvents were deuterated methanol ($CD_3OD$). Chemical shifts were given in $10^{-6}$ (ppm).

MS was determined by a FINNIGAN LCQAd (ESI) mass spectrometer (manufacturer: Thermo, type: Finnigan LCQ advantage MAX).

Thin-layer silica gel plate was Yantai Huanghai HSGF254 or Qingdao GF254 silica gel plate. The plate used in TLC was 0.15 mm~0.2 mm, and the plate used in purification of products was 0.4 mm~0.5 mm.

Column chromatography generally used Yantai Huanghai 200-300 mesh silica gel as carrier.

The starting materials of the present invention are known and purchased from ABCR GmbH & Co. KG, Acros Organics, Aldrich Chemical Company, Accela ChemBio Inc, Darui Finechemical Co., Ltd and so on, or they can be prepared by the conventional synthesis methods in the art.

Unless otherwise stated, the following reactions were performed under nitrogen atmosphere.

"Nitrogen atmosphere" refers to that the reaction flask is equipped with a nitrogen balloon of about 1 L.

"Hydrogen atmosphere" refers to that the reaction flask is equipped with a hydrogen balloon of about 1 L.

Unless otherwise stated, the solution used in following reactions refers to aqueous solution.

Unless otherwise stated, the reaction temperature was room temperature.

The appropriate room temperature was 20° C.~30° C.

The reactions process of the examples was monitored by thin layer chromatography (TLC). The developing solvent system comprised dichloromethane and methanol system, hexane and ethyl acetate system, petroleum ether and ethyl acetate system and acetone. The ratio of the volume of the solvent was adjusted according to the polarity of the compounds.

The elution system of column chromatography comprised: A: dichloromethane and methanol system, B: hexane and ethyl acetate system. The ratio of the volume of the solvent was adjusted according to the polarity of the compounds and sometimes ammonia or acetic acid was also added.

HPLC refers to High Performance Liquid Chromatography.

HPLC was determined by Agilent 2695-2996 high performance liquid chromatographic instrument (Gimini C18 150× 4.6 mm column).

HPLC test conditions: running time: 30 minutes; column temperature: 30° C.; PDA: 230 nm; Mobile phase: methanol: water (0.1% aqueous ammonia)=25:75; flow rate: 1.0 mL/min.

Example 1

(R)-7-[3-Amino-4-(2,4,5-trifluorophenyl)-butanoyl]-3-trifluoromethyl-5,6,7,8-tetrahydro-imidazo[1,5-a]pyrazine-1-carboxylic acid hydrochloride

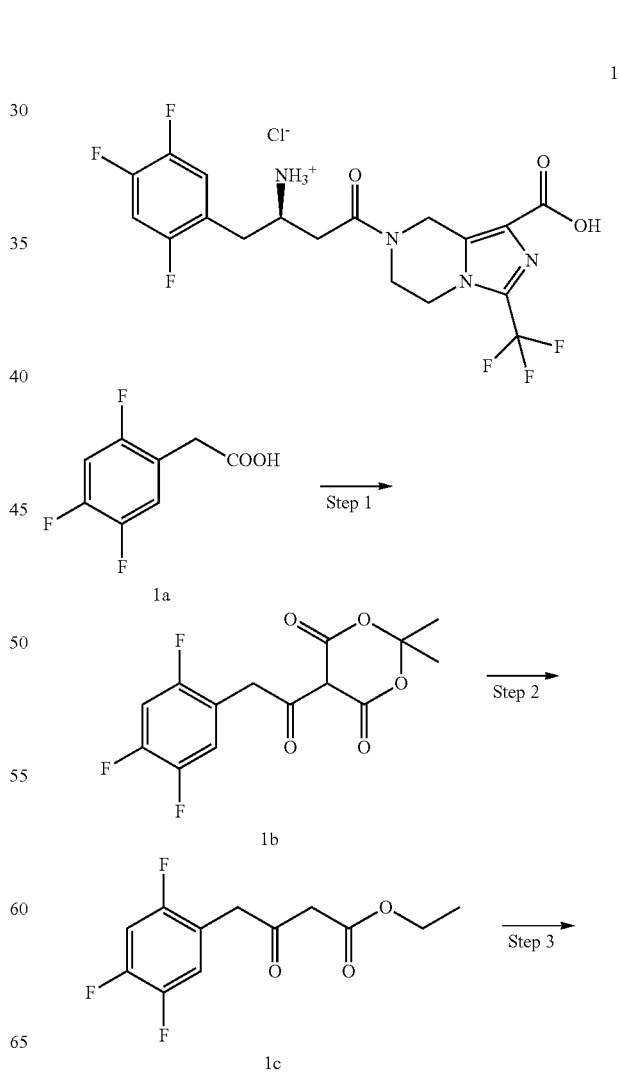

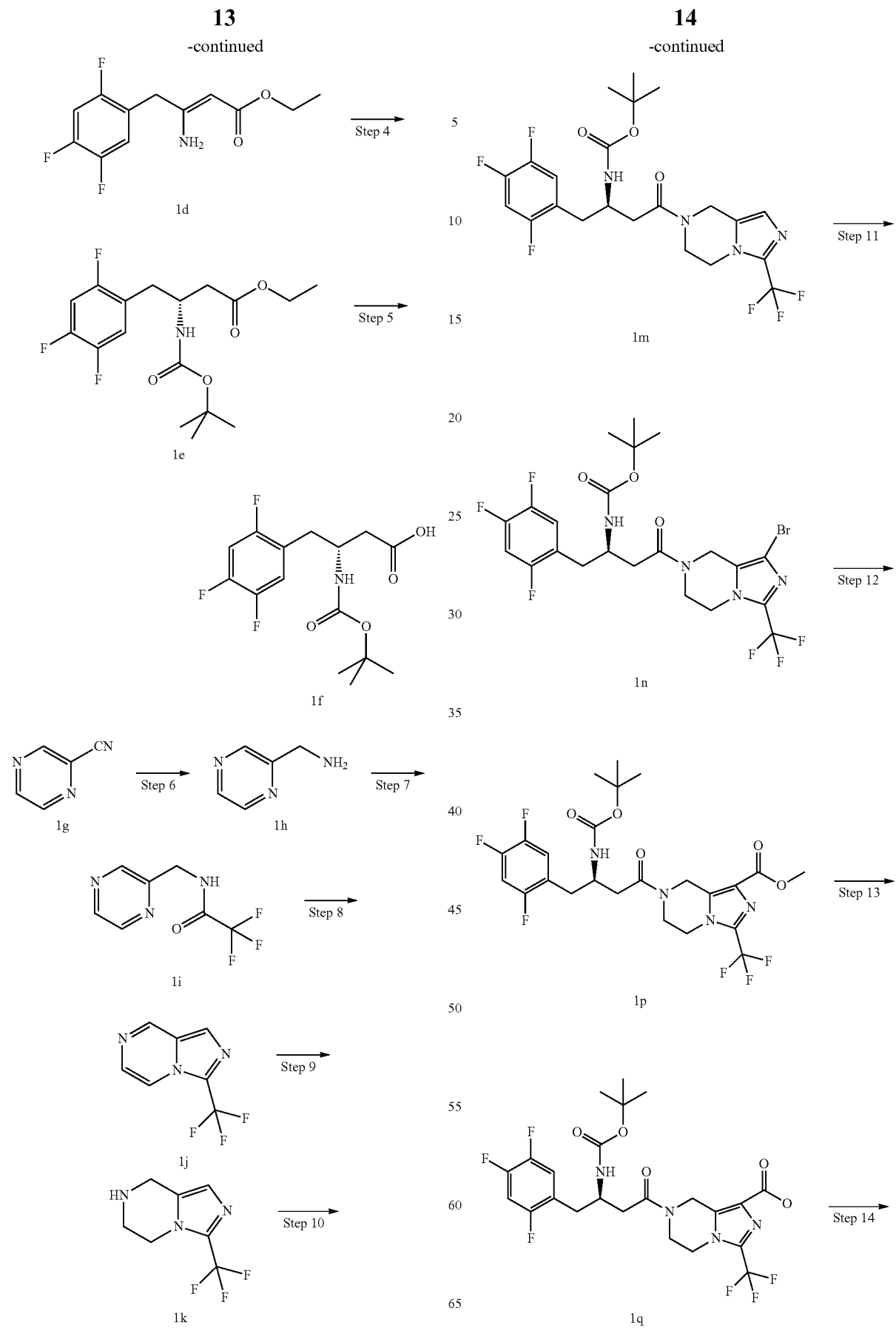

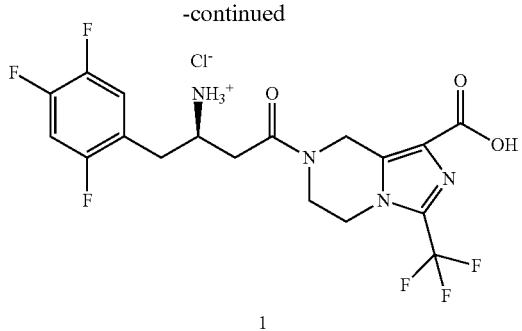

1

Step 1

2,2-Dimethyl-5-[2-(2,4,5-trifluorophenyl)-acetyl]-[1,3]dioxane-4,6-dione 2,2-Dimethyl-[1,3]dioxane-4,6-dione (5.69 g, 39.5 mmol) was dissolved in 400 mL of dichloromethane under stirring, followed by addition of 2,4,5-trifluorophenyl acetic acid 1a (7.15 g, 37.6 mmol) and 4-dimethylaminopyridine (7.35 g, 60.2 mmol) in an ice-water bath. Then a suspension of 1-(3-dimethylaminopropyl)-3-ethylcarbodiimide hydrochloride (8.28 g, 43.2 mmol) in 250 mL of dichloromethane was added dropwise slowly. After stirring at room temperature for 36 hours, the reaction mixture was washed with the solution of 5% potassium bisulfate (250 mL×7) and saturated brine (250 mL×2), dried over anhydrous magnesium sulfate, filtered and concentrated under reduced pressure to obtain the title compound 2,2-dimethyl-5-[2-(2,4,5-trifluorophenyl)-acetyl]-[1,3]dioxane-4,6-dione 1b (11.4 g, yield 96%) as a white solid. MS m/z (ESI): 315.5 [M−1].

Step 2

Ethyl 3-oxo-4-(2,4,5-trifluoro-phenyl)-butyrate 2,2-Dimethyl-5-[2-(2,4,5-trifluoro-phenyl)-acetyl]-[1,3]dioxane-4,6-dione 1b (15.72 g, 49.6 mmol) was dissolved in 280 mL of ethanol under stirring, then the reaction mixture was heated to 70° C. in an oil bath for 12 hours. After cooling to room temperature, the mixture was concentrated under reduced pressure. The resulting residue was purified by silica gel column chromatography with system B as eluant to obtain the title compound ethyl 3-oxo-4-(2,4,5-trifluoro-phenyl)-butyrate 1c (12 g, yield 88%) as a yellow oil. MS m/z (ESI): 259 [M−1].

Step 3

Ethyl 3-amino-4-(2,4,5-trifluorophenyl)-but-2-enoate

Ethyl 3-oxo-4-(2,4,5-trifluoro-phenyl)-butyrate 1c (24.6 g, 94.5 mmol) was dissolved in 240 mL of methanol, and ammonium acetate (36.4 g, 473 mmol) was added to the solution. The reaction mixture was heated to reflux for 3 hours. The reaction mixture was concentrated under reduced pressure, and then 100 mL of water was added to the residues. The mixture was extracted with ethyl acetate (200 mL×3), and the combined organic phase was washed with 200 mL of saturated brine, dried over anhydrous magnesium sulfate, filtered and concentrated under reduced pressure to obtain a light yellow solid. The resulting solid was dissolved in 50 mL of ethyl acetate at 80° C., and then 50 mL of n-hexane and seed-crystal were added to the solution. The mixture was cooled to room temperature, and half an hour later, 100 mL of n-hexane was added. The mixture was stored in refrigerator for 12 hours and then filtered to obtain the title compound ethyl 3-amino-4-(2,4,5-trifluoro-phenyl)-but-2-enoate 1d (19.5 g, yield 80%) as a white solid. MS m/z (ESI): 260.1 [M+1].

Step 4

Ethyl 3-tert-butoxycarbonylamino-4-(2,4,5-trifluoro-phenyl)-butyrate

Ethyl 3-amino-4-(2,4,5-trifluoro-phenyl)-but-2-enoate 1d (4.1 g, 15.8 mmol) was added into an autoclave, followed by addition of 70 mL of methanol, di-tert-butyl dicarbonate (3.8 g, 17.4 mmol), chloro(1,5-cyclooctadiene)rhodium (I) dimer (32 mg, 0.0632 mmol) and (R)-1-[(S)-2-(diphenyl phosphino)ferrocenyl]-ethyl-tert-butylphosphine (68 mg, 0.13 mmol). The reaction mixture was reacted in hydrogen atmosphere for 24 hours under 6.67 atmosphere at 30° C. The mixture was filtered and the filtrate was concentrated under reduced pressure. Then 34 mL of methanol was added to the residues at 50° C., followed by addition of 12 mL of water after total dissolved. After cooling to room temperature, the mixture was stored in the refrigeratory for 12 hours and then filtered. The solid product was washed with the mixture of methanol/water (v:v=1:1), dried in vacuo to obtain the title compound ethyl 3-tert-butoxycarbonyl-amino-4-(2,4,5-trifluoro-phenyl)-butyrate 1e (4 g, yield 70%) as a light yellow solid. MS m/z (ESI): 362.4 [M+1].

Step 5

(R)-3-tert-Butoxycarbonylamino-4-(2,4,5-trifluoro-phenyl)-butyric acid

Refer to the common known method *Tetrahedron Asymmetry*, 2006, 17(2), 205-209. 3-tert-Butoxycarbonylamino-4-(2,4,5-trifluoro-phenyl)-butyric acid ethyl ester 1e (10 g, 27.7 mmol) and sodium hydroxide (3.32 g, 83.1 mmol) were dissolved in 150 mL of the mixture of methanol and water (v:v=1:1). The reaction mixture was stirred at 40-45° C. for 1-1.5 hours, then part of the solution was evaporated under reduced pressure. The residues were added with a little of water, then the pH was adjusted to 2-3 with 1 M hydrochloric acid in an ice-water bath. The mixture was extracted with ethyl acetate (200 mL×3), and the combined organic phase was washed with 200 mL of saturated brine, dried over anhydrous sodium sulfate, filtered and concentrated under reduced pressure, and then the residues were recrystallized from ethyl acetate/n-hexane to obtain the title compound (R)-3-tert-butoxycarbonylamino-4-(2,4,5-trifluoro-phenyl)-butyric acid 1f (9.2 g) as a white solid, which was directly used in the next step. MS m/z (ESI): 332.3 [M−1].

Step 6

C-Pyrazin-2-yl-methylamine

Pyrazine-2-carbonitrile 1 g (10.5 g, 100 mmol) was dissolved in 150 mL of 1,4-dioxane, then Raney nickel (1.0 g) was added into a 250 mL autoclave. The reaction mixture was reacted in hydrogen atmosphere for 8 hours under 40 atmosphere at 60° C. and filtered and concentrated under reduced pressure to obtain the title compound C-pyrazin-2-yl-methyl amine 1h (10.7 g, yield 98%) as a brown oil. MS m/z (ESI): 110 [M+1].

Step 7

2,2,2-Trifluoro-N-pyrazin-2-ylmethyl-acetamide

C-Pyrazin-2-yl-methylamine 1 h (10.9 g, 100 mmol) was added into a reaction flask, then 20 mL of trifluoroacetic anhydride was added dropwise slowly within an hour at 0° C. in an ice-water bath. The reaction mixture was reacted at room temperature for 2 hours. Then the mixture was concentrated under reduced pressure. The resulting residues were purified by silica gel column chromatography with system A as eluant to obtain the title compound 2,2,2-trifluoro-N-pyrazin-2-ylmethyl-acetamide 1i (21.0 g) as a brown oil. MS m/z (ESI): 206.1 [M+1].

Step 8

3-Trifluoromethyl-imidazo[1,5-a]pyrazine 2,2,2-Trifluoro-N-pyrazin-2-ylmethyl-acetamide 1i (21.0 g, 100 mmol) was added into a reaction flask, followed by addition of 100 mL of phosphorus oxychloride. After stirring for 30 minutes, phosphorous pentoxide (17.8 g, 125 mmol) was added to the solution. The reaction mixture was heated to reflux for 5 hours. The mixture was concentrated under reduced pressure, and the reaction system was quenched with deionized water. The mixture was adjusted to pH 5-6 with 20% sodium hydroxide solution in an ice-water bath and then extracted with ethyl acetate (250 mL×4). The combined organic phase was dried over anhydrous magnesium sulfate, filtered and concentrated under reduced pressure. The resulting residues were purified by silica gel column chromatography with system A as eluant to obtain the title compound 3-trifluoromethyl-imidazo[1,5-a]pyrazine 1j (12.0 g, yield 65%) as a yellow solid. MS m/z (ESI): 188.0 [M+1]. $^1$H NMR (400 MHz, CDCl$_3$, ppm): δ 9.15 (s, 1H), 8.06 (d, 1H), 7.92 (s, 1H), 7.81 (d, 1H).

Step 9

3-Trifluoromethyl-5,6,7,8-tetrahydro-imidazo[1,5-a]pyrazine

3-Trifluoromethyl-imidazo[1,5-a]pyrazine 1j (12.0 g, 64.2 mmol) was dissolved in 150 mL of anhydrous ethanol, then 10% Pd/C (500 mg) was added to the solution. The reaction mixture was stirred at room temperature under a hydrogen atmosphere for 12 hours. The reaction solution was filtered through a pad of coarse silica gel and the filtrate was concentrated under reduced pressure to obtain the title compound 3-trifluoromethyl-5,6,7,8-tetrahydro-imidazo[1,5-a]pyrazine 1k (12.2 g, yield 99%) as a brown solid. $^1$H NMR (400 MHz, CDCl$_3$, ppm): δ 6.84 (s, 1H), 4.10 (m, 4H), 3.26 (m, 2H), 1.81 (s, 1H).

Step 10 tert-Butyl (R)-[3-oxo-1-(2,4,5-trifluoro-benzyl)-3-(3-trifluoromethyl-5,6-dihydro-8H-imidazo[1,5-a]pyrazin-7-yl)-propyl]-carbamate (R)-3-tert-Butoxycarbonylamino-4-(2,4,5-trifluoro-phenyl)-butyric acid 1f (8.6 g, 45 mmol) and 9.4 mL of triethylamine were dissolved in 300 mL of dichloromethane. After stirring for 5 minutes, 3-trifluoromethyl-5,6,7,8-tetrahydro-imidazo[1,5-a]pyrazine 1k (15.0 g, 45 mmol) and bis(2-oxo-3-oxazolidinyl)phosphinic chloride (17.1 g, 67.3 mmol) were added to the solution successively. The reaction mixture was reacted for 2 hours and then concentrated under reduced pressure. The resulting residues were purified by silica gel column chromatography with system B as eluant to obtain the title compound tert-Butyl (R)-[3-oxo-1-(2,4,5-trifluoro-benzyl)-3-(3-trifluoromethyl-5,6-dihydro-8H-imidazo[1,5-a]pyrazin-7-yl)-propyl]-carbamate 1m (20.0 g, yield 88%) as a white solid. $^1$H NMR (400 MHz, CD$_3$OD, ppm): δ 7.25 (m, 1H), 7.11 (m, 1H), 7.032 (s, 1H), 4.93 (m, 2H), 4.35 (m, 3H), 4.05 (m, 2H), 2.99 (m, 2H), 2.73 (m, 2H), 1.34 (s, 9H).

Step 11 tert-Butyl(R)-[3-oxo-1-(2,4,5-trifluoro-benzyl)-3-(1-bromo-3-trifluoromethyl-5,6-dihydro-8H-imidazo[1,5-a]pyrazin-7-yl)-propyl]-carbamate tert-Butyl(R)-[3-oxo-1-(2,4,5-trifluoro-benzyl)-3-(3-trifluoromethyl-5,6-dihydro-8H-imidazo[1,5-a]pyrazin-7-yl)-propyl]-carbamate 1m (20.0 g, 39.6 mmol) was dissolved in 300 mL of anhydrous ethanol, and N-bromosuccinimide (14.1 g, 79.2 mmol) was then added to the solution. After stirring for an hour, potassium carbonate (10.9 g, 79.2 mmol) and di-tert-butyl dicarbonate (8.6 g, 39.6 mmol) were added to the mixture, and the mixture was stirred for another one hour. The reaction mixture was filtered through a pad of coarse silica gel, and then the filtrate was concentrated under reduced pressure. The resulting residues were purified by silica gel column chromatography with system B as eluant to obtain the title compound tert-butyl (R)-[3-oxo-1-(2,4,5-trifluoro-benzyl)-3-(1-bromo-3-trifluoromethyl-5,6-dihydro-8H-imidazo[1,5-a]pyrazin-7-yl)-propyl]-carbamate 1n (20.0 g, yield 86%) as a white solid. $^1$HNMR (400 MHz, CDCl$_3$, ppm): δ 7.063 (m, 1H), 6.88 (m, 1H), 4.72 (s, 1H), 4.56 (s, 1H), 4.13 (m, 3H), 3.88 (m, 2H), 2.94 (m, 2H), 2.62 (m, 2H), 1.36 (s, 9H).

Step 12

Methyl(R)-7-[3-tert-butoxycarbonylamino-4-(2,4,5-trifluoro-phenyl)-butyryl]-3-trifluoro methyl-5,6,7,8-tetrahydro-imidazo[1,5-a]pyrazine-1-formate Refer to *Journal of Organometallic Chemistry*, 1985, 285 (1-3), 293-303. Octacarbonyldicobalt (4.02 g, 11.76 mmol), ethyl chloroacetate (0.71 g, 5.88 mmol), potassium carbonate (1.62 g, 11.76 mmol) and 50 mL of methanol were added into the reaction flask. After stirring for 5 minutes, tert-butyl (R)-[3-oxo-1-(2,4,5-trifluoro-benzyl)-3-(1-bromo-3-trifluoromethyl-5,6-dihydro-8H-imidazo[1,5-a]pyrazin-7-yl)-prop yl]-carbamate 1n (2.3 g, 3.92 mmol) was added. The reaction mixture was stirred at 60° C. for 2 hours and then concentrated under reduced pressure. The resulting residues were purified by silica gel column chromatography with system B as eluant to obtain the title compound methyl (R)-7-[3-tert-butoxycarbonylamino-4-(2,4,5-trifluoro-phenyl)-butyryl]-3-trifluoromethyl-5,6,7,8-tetrahydro-imidazo[1,5-a]pyrazine-1-formate 1p (1.1 g, yield 50%) as a white solid. MS m/z (ESI): 565.0 [M+1].

Step 13

(R)-7-[3-tert-Butoxycarbonyl-4-(2,4,5-trifluorophenyl)butanoyl]-3-trifluoromethyl-5,6,7,8-tetrahydro-imidazo[1,5-a]pyrazine-1-carboxylic acid Methyl(R)-7-[3-tert-butoxycarbonylamino 5-trifluoro-phenyl)-butyryl]-3-trifluoro methyl-5,6,7,8-tetrahydro-imidazo[1,5-a]pyrazine-1-formate 1p (1.8 g, 3.2 mmol) was dissolved in 50 mL of methanol, followed by addition of 10 mL of aqueous sodium hydroxide (4 M). The reaction mixture was stirred for 1 hours. The reaction mixture was adjusted to pH=3-5 with 2 M hydrochloric acid in an ice bath. The mixture was extracted with ethyl acetate (100 mL×3). The combined organic phase was dried over anhydrous magnesium sulfate, filtered and concentrated under reduced pressure to obtain the title compound (R)-7-[3-tert-butoxycarbonyl-4-(2,4,5-trifluorophenyl)butanoyl]-3-trifluoromethyl-5,6,7,8-tetrahydro-imidazo[1,5-a]pyrazine-1-carboxylic acid 1q (1.76 g, yield 100%) as a light yellow solid. MS m/z (ESI): 550.9 [M+1]. $^1$H NMR (400 MHz, CD$_3$OD, ppm): δ 7.29-7.23 (m, 1H), 7.121-7.08 (m, 1H), 5.15-5.03 (m, 2H), 4.41-4.06 (m, 5H), 2.98-2.77 (m, 4H), 1.42-1.26 (m, 9H).

Step 14

(R)-7-[3-Amino-4-(2,4,5-trifluorophenyl)butanoyl]-3-(trifluoromethyl)-5,6,7,8-tetrahydroimidazo[1,5-a]pyrazine-1-carboxylic acid hydrochloride (R)-7-[3-tert-Butoxycarbonyl-4-(2,4,5-trifluorophenyl)butanoyl]-3-trifluoromethyl-5,6,7,8-tetrahydroimidazo[1,5-a]pyrazine-1-carboxylic acid 1q (1.76 g, 3.2 mmol) was added to the reaction flask followed by addition of 10 mL of ethyl acetate hydrogen chloride. The reaction mixture was stirred for 1 hour and then concentrated under reduced pressure to obtain the title compound (R)-7-[3-amino-4-(2,4,5-trifluoro-phenyl)-butanoyl]-3-trifluoromethyl-5,6,7,8-tetrahydro-imidazo[1,5-a]pyrazine-1-carboxylic acid hydrochloride 1 (1.56 g, yield 100%) as a white solid. MS m/z (ESI): 451.2 [M+1]. $^1$H NMR (400 MHz, CD$_3$OD, ppm): δ 7.42-7.37 (m, 1H), 7.28-7.23 (m, 1H), 5.19-5.05 (m, 2H), 4.36-4.29 (m, 1H), 4.15-4.00 (m, 2H), 3.94-3.93 (m, 2H), 3.21-2.88 (m, 2H), 2.86-2.81 (m, 2H).

Example 2

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid phosphate

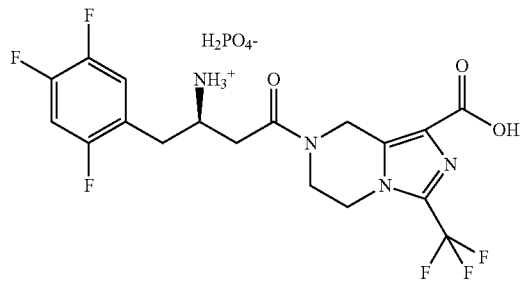

2

(R)-7-[3-Amino-4-(2,4,5-trifluoro-phenyl)-butanoyl]-3-trifluoromethyl-5,6,7,8-tetrahydroimidazo[1,5-a]pyrazine-1-carboxylic acid hydrochloride 1 (1.45 g, 2.97 mmol) was dissolved in 14 mL of dichloromethane. Then the mixture was washed with 6 mL of aqueous sodium bicarbonate and the aqueous layer was extracted with 5.6 mL of dichloromethane. The combined organic phase was washed with 6 mL of saturated brine, dried over anhydrous sodium sulfate, filtered and concentrated under reduced pressure to obtain oil residues (1.38 g). The residues were dissolved in 40 mL of isopropyl alcohol followed by addition of a solution of 85% phosphoric acid (342.8 mg, 2.97 mmol) in 2 mL of isopropyl alcohol under stirring until solid precipitation. After stirring for 2 hours the mixture was filtered and the filtered cake was washed with isopropyl alcohol and dried under reduce pressure at 40° C. to obtain the crude compound (1.44 g, 88.6%). The crude compound (1.44 g, 2.63 mmol) was dissolved in 26 mL of isopropyl alcohol and stirred for 1 hour. The mixture was filtered and the filtered cake was washed with isopropyl alcohol. The solid was dissolved in deionized water. The mixture was concentrated under reduced pressure at 40° C. and dried in vacuo at 40° C. to obtain the title compound (R)-7-[3-amino-4-(2,4,5-trifluorophenyl) butanoyl]-3-trifluoromethyl-5,6,7,8-tetrahydro-imidazo[1,5-a]pyrazine-1-carboxylic acid phosphate 2 (1.33 g, 92.6%) as a white powder. MS m/z (ESI): 451.2 [M+1]. $^1$H NMR (400 MHz, CD$_3$OD, ppm): δ 7.36-7.42 (m, 1H), 7.19-7.25 (m, 1H), 5.01-5.15 (m, 2H), 4.24-4.34 (m, 2H), 4.06-4.11 (m, 1H), 3.91-3.98 (m, 1H), 3.07-3.12 (m, 2H), 2.8-3.09 (m, 2H).

Example 3

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid

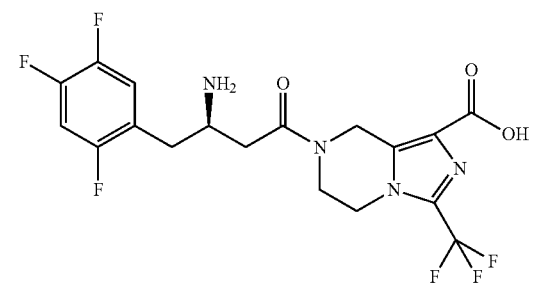

3

(R)-7-[3-Amino-4-(2,4,5-trifluoro-phenyl)-butanoyl]-3-trifluoromethyl-5,6,7,8-tetrahydroimidazo[1,5-a]pyrazine-1-carboxylic acid hydrochloride 1 (1.02 g, 2.1 mmol) was dissolved in 30 mL of methanol followed by addition of aqueous sodium hydroxide (2.1 mL, 2.1 mmol). The reaction was stirred for 15 minutes. The reaction mixture was concentrated under reduced pressure and the resulting solid was dissolved in 15 mL of the solvent mixture of dichloromethane/methanol (v:v=1:3). The mixture was filtered and concentrated under reduced pressure to obtain the title compound (R)-7-[3-amino-4-(2,4,5-trifluorophenyl)butanoyl]-3-trifluoromethyl-5,6,7,8-tetrahydro-imidazo[1,5-a]pyrazine-1-carboxylic acid 3 (943 mg, 100%) as a white solid. HPLC: 99.89%. MS m/z (ESI): 451.2 [M+1]. $^1$H NMR (400 MHz, CD$_3$OD, ppm): δ 7.32-7.41 (m, 1H), 7.11-7.21 (m, 1H), 5.00-5.07 (m, 2H), 4.16-4.24 (m, 2H), 4.05-4.08 (m, 1H), 3.85-3.97 (m, 2H), 3.05-3.17 (m, 2H), 2.91-2.93 (m, 2H).

Example 4

Sodium (R)-7-[3-amino-4-(2,4,5-trifluorophenyl)butanoyl]-3-trifluoromethyl-5,6,7,8-tetrahydro-imidazo[1,5-a]pyrazine-1-carboxylate

4

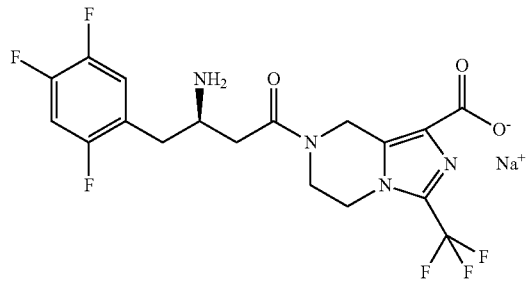

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 5 mL of methanol followed by addition of aqueous sodium hydroxide (0.44 mL, 0.22 mmol). The reaction was stirred for 15 minutes. The reaction mixture was concentrated under reduced pressure to obtain the title compound sodium (R)-7-[3-amino-4-(2,4,5-trifluorophenyl)butanoyl]-3-trifluoromethyl-5,6,7,8-tetrahydro-imidazo[1,5-a]pyrazine-1-carboxylate 4 (104 mg, 99.7%) as a white solid. HPLC: 99.65%. MS m/z (ESI): 451.2 [M+1]. $^1$H NMR (400 MHz, CD$_3$OD, ppm): δ 7.26-7.30 (m, 1H), 7.08-7.13 (m, 1H), 5.00-5.20 (m, 2H), 4.26-4.27 (m, 2H), 4.00-4.11 (m, 2H), 3.44-3.48 (m, 1H), 2.72-2.83 (m, 2H), 2.59-2.60 (m, 2H).

Example 5

Lithium (R)-7-[3-amino-4-(2,4,5-trifluorophenyl)butanoyl]-3-trifluoromethyl-5,6,7,8-tetrahydro-imidazo[1,5-a]pyrazine-1-carboxylate

5

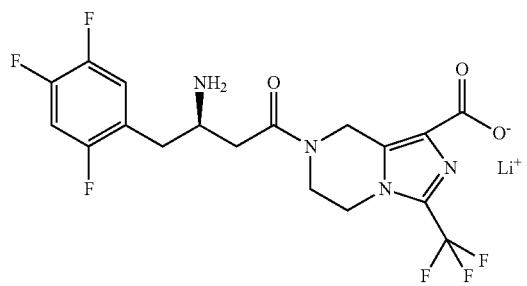

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 5 mL of methanol followed by addition of aqueous lithium hydroxide solution (0.44 mL, 0.22 mmol). The reaction was stirred for 15 minutes. The reaction mixture was concentrated under reduced pressure to obtain the title compound lithium (R)-7-[3-amino-4-(2,4,5-trifluorophenyl)butanoyl]-3-trifluoromethyl-5,6,7,8-tetrahydro-imidazo[1,5-a]pyrazine-1-carboxylate 5 (48 mg, 98.6%) as a white solid. HPLC: 99.66%. MS m/z (ESI): 451.2 [M+1]. $^1$H NMR (400 MHz, CD$_3$OD, ppm): δ 7.31-7.38 (m, 1H), 7.13-7.22 (m, 1H), 5.07-5.27 (m, 2H), 4.26-4.36 (m, 2H), 4.01-4.15 (m, 2H), 3.53-3.60 (m, 1H), 2.80-2.91 (m, 2H), 2.59-2.72 (m, 2H).

Example 6

Potassium (R)-7-[3-amino-4-(2,4,5-trifluorophenyl)butanoyl]-3-trifluoromethyl-5,6,7,8-tetrahydro-imidazo[1,5-a]pyrazine-1-carboxylate

6

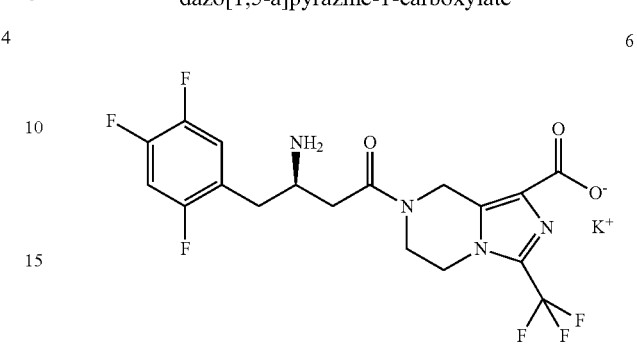

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 5 mL of methanol followed by addition of aqueous potassium hydroxide (0.44 mL, 0.22 mmol). The reaction was stirred for 15 minutes. The reaction mixture was concentrated under reduced pressure to obtain the title compound potassium (R)-7-[3-amino-4-(2,4,5-trifluorophenyl)butanoyl]-3-trifluoromethyl-5,6,7,8-tetrahydro-imidazo[1,5-a]pyrazine-1-carboxylate 6 (108 mg, 100%) as a white solid. HPLC: 92.78%. MS m/z (ESI): 451.2 [M+1]. $^1$H NMR (400 MHz, CD$_3$OD, ppm): δ 7.31-7.38 (m, 1H), 7.14-7.23 (m, 1H), 5.07-5.27 (m, 2H), 4.26-4.36 (m, 2H), 4.01-4.15 (m, 2H), 3.52-3.60 (m, 1H), 2.80-2.92 (m, 2H), 2.59-2.74 (m, 2H).

Example 7

Calcium (R)-7-[3-amino-4-(2,4,5-trifluorophenyl)butanoyl]-3-trifluoromethyl-5,6,7,8-tetrahydro-imidazo[1,5-a]pyrazine-1-carboxylate

7

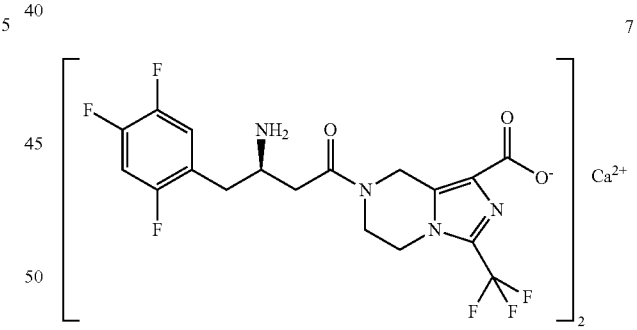

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 10 mL of methanol followed by addition of aqueous calcium hydroxide solution (8.1 mg, 0.11 mmol). The mixture was stirred for 20 hours. The reaction mixture was concentrated under reduced pressure to obtain the title compound calcium (R)-7-[3-amino-4-(2,4,5-trifluorophenyl)butanoyl]-3-trifluoromethyl-5,6,7,8-tetrahydro-imidazo[1,5-a]pyrazine-1-carboxylate 7 (103 mg, 100%) as a white solid. HPLC: 99.60%. MS m/z (ESI): 451.2 [M+1]. $^1$H NMR (400 MHz, CD$_3$OD, ppm): δ 7.28-7.34 (m, 1H), 7.11-7.21 (m, 1H), 5.10-5.21 (m, 2H), 4.22-4.36 (m, 2H), 4.03-4.09 (m, 2H), 3.55-3.59 (m, 1H), 2.76-2.85 (m, 2H), 2.60-2.71 (m, 2H).

Example 8

Triethylammonium (R)-7-[3-amino-4-(2,4,5-trifluorophenyl)butanoyl]-3-(trifluoromethyl)-5,6,7,8-tetrahydro-imidazo[1,5-a]pyrazine-1-carboxylate

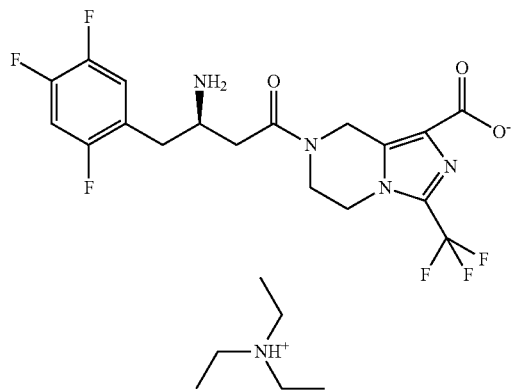

8

(R)-7-[3-Amino-4-(2,4,5-trifluorophenyl)butanoyl]-3-(trifluoromethyl)-5,6,7,8-tetrahydroimidazo[1,5-a]pyrazine-1-carboxylic acid 3 (100 mg, 0.22 mmol) was dissolved in 5 mL of methanol followed by addition of a solution of triethylamine in methanol (0.767 mL, 0.22 mmol, the solution was prepared by adding 1 mL triethylamine to methanol to form 25 mL solution of triethylamine in methanol). The mixture was stirred for 40 hours. The reaction mixture was concentrated under reduced pressure to obtain the title compound triethylammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate 8 (112 mg, 99.8%) as a white solid. HPLC: 99.8%. MS m/z (ESI): 451.2 [M+1]. $^1$H NMR (400 MHz, CD$_3$OD, ppm): δ 7.28-7.35 (m, 1H), 7.10-7.19 (m, 1H), 5.03-5.13 (m, 2H), 4.17-4.25 (m, 2H), 3.88-4.08 (m, 2H), 3.70-3.73 (m, 1H), 3.12-3.17 (m, 6H), 2.93-2.95 (m, 2H), 2.71-2.80 (m, 2H), 1.27-1.30 (m, 9H).

Example 9

2-Hydroxyethylammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate

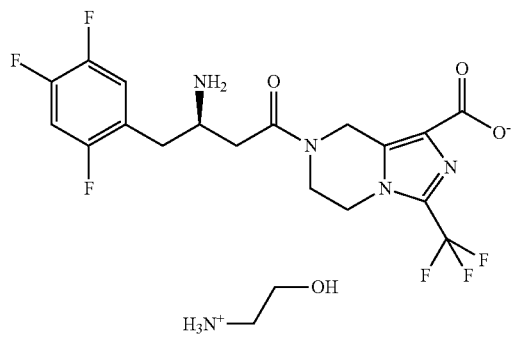

9

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 5 mL of methanol followed by addition of a solution of ethanolamine in methanol (0.33 mL, 0.22 mmol, the solution was prepared by adding 1 mL ethanolamine to methanol to form 25 mL solution of ethanolamine in methanol). The mixture was stirred for 40 hours. The reaction mixture was concentrated under reduced pressure to obtain the title compound 2-hydroxyethylammonium (R)-7-[3-amino-4-(2,4,5-trifluorophenyl) butanoyl]-3-trifluoromethyl-5,6,7,8-tetrahydro-imidazo[1,5-a]pyrazine-1-carboxylate 9 (114 mg, 99.62%) as a white solid. HPLC: 99.62%. MS m/z (ESI): 451.2 [M+1]. $^1$H NMR (400 MHz, CD$_3$OD, ppm): δ 7.27-7.32 (m, 1H), 7.07-7.16 (m, 1H), 4.96-5.17 (m, 2H), 4.12-4.26 (m, 2H), 3.91-4.09 (m, 2H), 3.70-3.72 (t, 2H), 3.56-3.57 (m, 1H), 2.95-2.98 (t, 2H), 2.80-2.89 (m, 2H), 2.58-2.70 (m, 2H).

Example 10

2-Hydroxyethyl(trimethyl)ammonium (R)-7-[3-Amino-4-(2,4,5-trifluorophenyl)-butanoyl]-3-trifluoromethyl-5,6,7,8-tetrahydro-imidazo[1,5-a]pyrazine-1-carboxylate

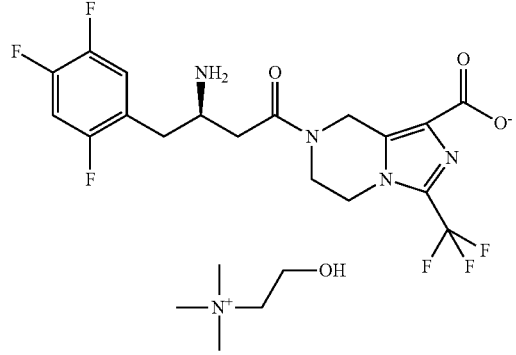

10

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 5 mL of methanol followed by addition of a solution of choline in methanol (1.55 mL, 0.22 mmol, the solution was prepared by addition of 1 mL choline in methanol to form 25 mL of choline in methanol). The mixture was stirred for 3 hours. The reaction mixture was concentrated under reduced pressure to obtain the title compound 2-hydroxyethyl(trimethyl)ammonium (R)-7-[3-amino-4-(2,4,5-trifluorophenyl)butanoyl]-3-trifluoromethyl-5,6,7,8-tetrahydro-imidazo[1,5-a]pyrazine-1-carboxylate 10 (120 mg, 98.5%) as a white solid. HPLC: 99.41%. MS m/z (ESI): 451.2 [M+1]. $^1$H NMR (400 MHz, CD$_3$OD, ppm): δ 7.23-7.30 (m, 1H), 7.06-7.15 (m, 1H), 4.99-5.19 (m, 2H), 4.19-4.26 (m, 2H), 3.89-4.07 (m, 4H), 3.60-3.71 (m, 1H), 3.50-3.55 (m, 2H), 3.21 (s, 9H), 2.72-2.84 (m, 2H), 2.55-2.66 (m, 2H).

Example 11

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S)-2-hydroxybutanedioic acid

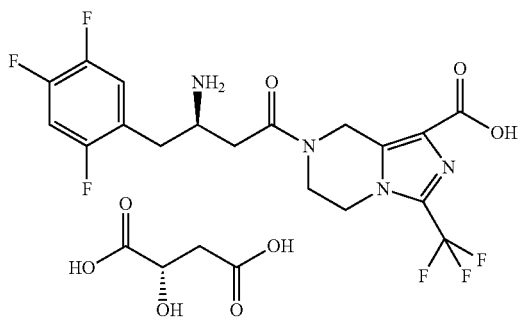

L-Malic acid (368 mg, 2.74 mmol) was dissolved in 25 mL of the solvent mixture of methanol/water (v:v=4:1) to form 0.11 M solution used by following steps. (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid 3 (100 mg, 0.22 mmol) was dissolved in 10 mL of methanol followed by addition of 2 mL of above mentioned solution. The mixture was stirred for 30 minutes. The reaction mixture was concentrated under reduced pressure to obtain the title compound (R)-7-[3-Amino-4-(2,4,5-trifluorophenyl)butanoyl]-3-(trifluoromethyl)-5,6,7,8-tetrahydro-imidazo[1,5-a]pyrazine-1-carboxylic acid (2S)-2-hydroxybutanedioic acid 11 (129 mg, 98.92%) as a white solid. HPLC: 98.92%. MS m/z (ESI): 451.1 [M+1]. $^1$H NMR (400 MHz, CD$_3$OD, ppm): δ 7.32-7.41 (m, 1H), 7.16-7.23 (m, 1H), 4.96-5.13 (m, 2H), 4.35-4.39 (m, 1H), 4.20-4.30 (m, 2H), 4.04-4.13 (m, 1H), 3.90-4.00 (m, 2H), 3.07-3.13 (m, 2H), 2.77-2.97 (m, 3H), 2.56-2.62 (m, 1H).

Example 12

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S,3S)-2,3-dihydroxybutanedioic acid

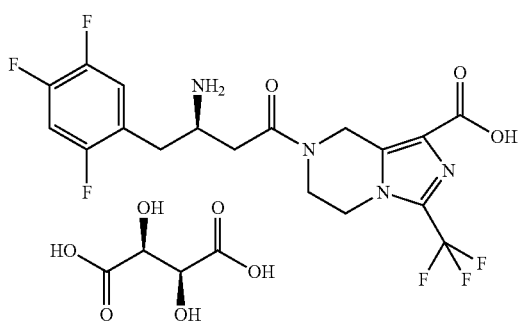

D-tartaric acid (413 mg, 2.75 mmol) was dissolved in 25 mL of the mixture solvent mixture of methanol/water (v:v=4:1) to form 0.11 M solution used by the following steps. (R)-7-[3-Amino-4-(2,4,5-trifluoro phenyl)butanoyl]-3-trifluoromethyl-5,6,7,8-tetrahydro-imidazo[1,5-a]pyrazine-1-carboxylic acid 3 (100 mg, 0.22 mmol) was dissolved in 10 mL of methanol followed by addition of 2 mL of above mentioned solution. The mixture was stirred for 30 minutes. The reaction mixture was concentrated under reduced pressure to obtain the title compound (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S,3S)-2,3-dihydroxy-butanedioic acid 12 (131 mg, 99%) as a white solid. HPLC: 99.35%. MS m/z (ESI): 451.1 [M+1]. $^1$H NMR (400 MHz, CD$_3$OD, ppm): δ 7.32-7.41 (m, 1H), 7.17-7.26 (m, 1H), 5.01-5.14 (m, 2H), 4.51 (s, 1H), 4.20-4.35 (m, 2H), 4.00-4.13 (m, 1H), 3.89-3.96 (m, 2H), 3.04-3.13 (m, 2H), 2.90-3.00 (m, 1H), 2.77-2.87 (m, 1H).

Example 13

(R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S)-2-amino-5-guanidino-pentanoic acid

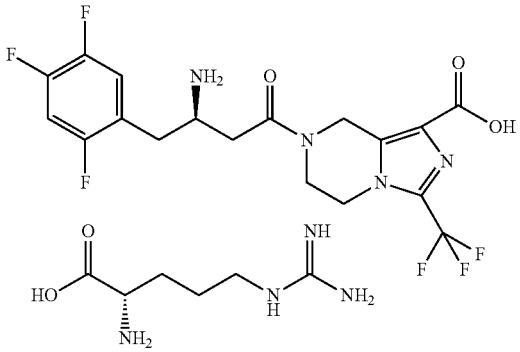

L-Arginine (239 mg, 1.37 mmol) was dissolved in 25 mL of the mixture solvent of methanol/water (v:v=4:1) to form 0.055 M solution used by the following steps. (R)-7-[3-Amino-4-(2,4,5-trifluorophenyl)butanoyl]-3-(trifluoromethyl)-5,6,7,8-tetrahydro-imidazo[1,5-a]pyrazine-1-carboxylic acid 3 (100 mg, 0.22 mmol) was dissolved in 15 mL of methanol followed by addition of 4 mL of above mentioned solution. The mixture was stirred for 4 hours. The reaction mixture was concentrated under reduced pressure to obtain the title compound (R)-7-[3-Amino-4-(2,4,5-trifluorophenyl)butanoyl]-3-trifluoromethyl-5,6,7,8-tetrahydro-imidazo[1,5-a]pyrazine-1-carboxylic acid (2S)-2-amino-5-guanidino-pentanoic acid 13 (139 mg, 100%) as a white solid. HPLC: 98.89%. MS m/z (ESI): 451.1 [M+1]. $^1$H NMR (400 MHz, CD$_3$OD, ppm): δ 7.24-7.32 (m, 1H), 7.09-7.14 (m, 1H), 4.98-5.18 (m, 2H), 4.25-4.28 (m, 1H), 4.18-4.19 (m, 1H), 3.93-4.04 (m, 2H), 3.50-3.54 (m, 2H), 3.18-3.23 (m, 2H), 2.76-2.87 (m, 2H), 2.58-2.69 (m, 2H), 1.77-1.90 (m, 2H), 1.67-1.75 (m, 2H).

Test Examples

Solubility Experiment

According to the conventional solubility measurement, the solubility of the test samples were determined in four different systems: phosphate buffer solution (PBS, pH=7.4), methanol, 0.1% hydrochloric acid and water. The results were showed in Table 1:

TABLE 1

| | Solubility Value (mg/mL) | | | |
|---|---|---|---|---|
| Example | PBS (pH 7.4) | methanol | 0.1% HCl | water |
| Example 1 | 18.6 | 31.3 | 17.2 | 20.9 |
| Example 2 | 20.2 | 37.5 | 32.5 | 26.1 |
| Example 3 | 7.0 | 32.7 | 20.5 | 9.2 |
| Example 4 | 57.4 | 46.7 | 94.8 | 43.5 |
| Example 5 | 60.5 | 50.3 | 100.6 | 40.2 |
| Example 8 | 0.2 | 20.1 | 8.3 | 0.5 |
| Example 9 | 0.3 | 35.2 | 12.6 | 1.0 |
| Example 10 | 1.2 | 40.3 | 15.2 | 1.5 |
| Example 11 | 19.5 | 5.4 | 32.6 | 22.2 |
| Example 12 | 12.3 | 0.5 | 33.8 | 19.5 |

Conclusion: the solubility of example 2, example 4 and example 5 was improved obviously.

Pharmacological Assays

The compounds of the present invention were tested to determine their DPP-IV, DPP-VIII, DPP-IX inhibition activity according to the following methods. The half inhibition concentrations $IC_{50}$ (the concentration of the test compound showing 50% inhibition to the enzyme activity) of each compound were determined by reaction test and calculation of the mixture of fixed amounts of enzyme and substrate with several different concentrations of the test compounds.

The compounds of the present invention were tested to determine the DPP-IV, DPP-VIII, DPP-IX inhibition activity in the following tests using Promega DPPIV-Glo™ Protease Assay (Cat No. G8350/G8351) Kit, wherein:
a. DPP-IV enzyme bought from Calbiochem, Catalog no. 317630;
b. DPP-VIII enzyme bought from Bioscience, Catalog no. 80080;
c. DPP-IX enzyme bought from Bioscience, Catalog no. 80090.

The preparation procedure of the conventional reagent such as DPPIV-Glo buffer, luciferin reagents needed in the test and the detail operation of the test can refer to the specifications of the kits. The assay was carried out as following steps:

The tested compounds were dissolved in DMSO to prepare a series of different concentrations of the test compound solution. DPPIV-Glo buffer and the freezing luciferin detection reagent were equilibrated to room temperature. The luciferin detection reagent was dissolved in moderate buffer in a brown flask to form a solution. Then DPP-IV-Glo. was dissolved in ultrapure water to give the appropriate concentration. The substrate solution and the luciferin detection reagent solution were mixed sufficiently in an appropriate ratio (the ratio of the invention is 1:49), and the mixture was layed at room temperature for 30-60 minutes. Tris buffer (2 mM, pH 8.0), the test compounds and DPP-IV (DPP-VIII or DPP-IX) were mixed and then transferred to a 96-well plate. Each test contains double-well of three-well control. The same volume of DMSO was added to the negative control and blank control. Then the 96-well plate was added with mixed solution of luciferin detection reagent and substrate to initiate the reaction. The 96-wells plate was incubated at room temperature on a plate shaker for 40 minutes after sealed. The strength of the fluorescent signal in each well was determined by microplate reader and the inhibition rate to the enzyme of the test compound at this concentration was calculated by the formula as following: inhibitory rate: IR=[1−(S−B)/(N−B)]*100%

S: value of the sample
B: value of the blank control
N: value of the negative control
$IC_{50}$ of the test compounds can be calculated by the inhibition rate at different concentration.

TABLE 2

| | $IC_{50}(\mu M)$ | | |
|---|---|---|---|
| Example | DPPIV | DPP8 | DPP9 |
| 1 | 0.021 | 87.9 | 63.6 |
| 2 | 0.015 | 399.7 | 185.0 |
| 3 | 0.013 | 235.7 | 125.4 |
| 4 | 0.022 | 77.3 | 42.3 |
| 5 | 0.025 | 80.5 | 50.6 |
| 8 | 0.021 | 152.5 | 135.6 |
| 9 | 0.012 | 113.7 | 128.3 |
| 10 | 0.023 | 210.1 | 165.6 |
| 11 | 0.009 | 279.7 | 180.1 |
| 12 | 0.012 | 243.8 | 135.5 |

Conclusion: the free form or the salts of each compounds exhibited excellent inhibition activity against DPP-IV. The compound of example 2 showed more preferable selectivity.

Pharmacokinetics Assay

Test Example 1

Pharmacokinetics Assay of the Compounds of the Present Invention

1. Test Objective

The compound of Example 3 was administrated intragastrically or tail vein injection to rats and the compounds of Example 1-4, Example 9 and Example 11-12 were administrated intragastrically to determine the drug concentration in plasma at different time points by LC/MS/MS measurement. The pharmacokinetics of the compounds of the present invention was studied and evaluated in rats. And the oral absolute bioavailability was investigated.

2. Protocol
2.1 Samples
Compounds of Example 1-4, Example 9 and Example 11-12.
2.2 Experimental Animals
28 healthy adult SD rats, male and female in half, were purchased from SINO-BRITSH SIPPR/BK LAB.ANIMAL LTD., CO, License number: SCXK (Shanghai) 2008-0016.
2.3 Instruments
API 4000 Q-trap Linear Ion Mass Spectrometer, Applied Biosystems Corp., USA;
Agilent 1200 high performance liquid chromatograph, Agilent Corp., USA;
2.4 Preparation of the Test Compounds
Vein injection group: the proper weighed test compound was dissolved in 0.5 mL of DMSO by ultrasound and then diluted with normal saline to 15 mL to form a 0.3 mg/mL solution.

Intragastrically administered group: the proper weighed test compound was dissolved in 0.5% CMC-Na by ultrasound to form a 0.3 mg/mL of suspension.
2.5 Administration
32 healthy adult SD rats, male and female in half, were divided into 8 groups so that each group consisted 4 rats. After an overnight fast, the rats were tail vein injected of the compound of Example 3 and intragastrically administered the compound of Example 3 and the salt thereof, at a dose of 3.0 mg/kg (calculated as the free base form) and a volume of 10 mL/kg.

2.6 Sample Collection

Blood samples (0.2 mL) of the rats in vein injection group were taken from eye socket at pre administration and at 2, 15, 30 minutes and 1.0, 2.0, 4.0, 6.0, 8.0, 12.0, 24.0 hours post administration, which were stored in heparinized tubes and centrifuged for 10 minutes at 3,500 rpm. The plasma samples were stored at −20° C. until analysis. The rats were fed 2 hours after administration.

Blood samples of the rats in intragastrically administered group were taken at pre administration and at 0.5, 1.0, 2.0, 3.0, 4.0, 6.0, 8.0, 12.0, 24.0 hours post administration. The samples were treated with the same method as mentioned above.

2.7 Analytical Methods

50 μL of internal standard solution and 150 μL of methanol were added to 50 μL of rat plasma obtained at various time points after administration. Then the mixture was mixed for 3 minutes using a vortexer and centrifuged for 10 minutes at 13,500 rpm. 10 μL of the supernatant was analyzed by LC/MS/MS.

2.8 Calculation of Pharmacokinetic Parameters

The compartmental model of pharmacokinetics was fitted for the test compounds and the major pharmacokinetic parameters were calculated by DAS 2.0 software in which $C_{max}$ and $t_{max}$ were the actually measured values. The absolute bioavailability was calculated by $AUC_{0-t}$ taken from post administration and vein injection.

2. Results of Pharmacokinetic Parameters

Pharmacokinetic Parameters of the compounds of the present invention were shown in Table 3.

Conclusion: compared with other compounds, pharmacokinetics and bioavailability of compound of Example 2 were improved obviously and the compound was obviously superior in pharmacokinetics.

2.3 Blood Sugar Level

The mice were administered according to above dose (the blank group was administrated with 5% DMSO aqueous solution) and the blood sugar value was measured (−15 minutes).

15 minutes after administration, the mice were administered of 4 g/kg of 20% glucose solution and the values of blood sugar were tested by Roche ACCU-CHEK at 0, 15, 30, 45, 60, 120 minutes.

2.4 The Results were Shown in Table 4:

TABLE 4

| Example No. | Hypoglycemic rate of blood sugar of 30 minutes after administration % (10 mg/kg) |
|---|---|
| 1 | 16.06 |
| 2 | 29.96 |
| 3 | 25.60 |
| 4 | 9.49 |
| 8 | 19.82 |
| 9 | 27.56 |
| 10 | 20.92 |
| 11 | 20.18 |
| 12 | 24.11 |

Conclusion: compared to other compounds, hypoglycemic effect of the compound of Example 2 had significant hypoglycemic effect.

TABLE 3

| Example | F (%) | $C_{max}$ (ng/mL) | $AUC_{0-t}$ (ng·h/mL) | $t_{1/2}$ (h) | $T_{max}$ (h) | MRT (h) | CL/F (L/h/kg) | Vz/F (l/kg) |
|---|---|---|---|---|---|---|---|---|
| 1 | 2.90 | 18.0 ± 7.5 | 66.6 ± 19.5 | 1.74 ± 0.16 | 2.50 ± 1.00 | 3.17 ± 0.36 | 45.6 ± 11.5 | 114 ± 27 |
| 2 | 8.63 | 66.6 ± 36.4 | 198.1 ± 57.4 | 1.69 ± 1.24 | 0.92 ± 0.58 | 4.05 ± 3.66 | 16.2 ± 4.55 | 41 ± 29.7 |
| 3 | 2.54 | 13.4 ± 5.6 | 58.3 ± 17.3 | 2.73 ± 0.73 | 1.00 ± 0.00 | 4.45 ± 1.01 | 51.7 ± 16.0 | 193 ± 38 |
|  | vein |  | 2295 ± 353 | 2.35 ± 1.90 | — | 0.22 ± 0.06 | 1.33 ± 0.20 | 6.05 ± 6.53 |
| 4 | 2.90 | 14.2 ± 2.0 | 66.6 ± 10.6 | 2.65 ± 0.94 | 1.75 ± 0.96 | 4.30 ± 0.60 | 43.7 ± 7.1 | 164 ± 56 |
| 9 | 4.06 | 25.1 ± 13.9 | 93.2 ± 36.4 | 3.18 ± 0.71 | 1.25 ± 0.50 | 4.34 ± 0.66 | 32.9 ± 10.0 | 155 ± 63 |
| 11 | 3.03 | 13.5 ± 3.9 | 69.5 ± 25.2 | 2.21 ± 0.69 | 1.63 ± 1.11 | 4.50 ± 1.32 | 46.6 ± 17.7 | 140 ± 39 |
| 12 | 3.25 | 17.0 ± 6.9 | 74.6 ± 21.7 | 2.54 ± 0.86 | 1.75 ± 0.50 | 4.23 ± 0.84 | 40.3 ± 9.9 | 154 ± 77 |

Preliminary Evaluation of Hypoglycemic Effects of the Compounds of the Present Invention 1. Test Objective To observe the effects on oral glucose tolerance of the compounds of Example 1-4 and Example 8-12 in normal ICR mice (SINO-BRITSH SIPPR/BK LAB.ANIMAL LTD., CO), the hypoglycemic effects in vivo have been evaluated using blood-glucose meter to measure and analyze the sugar content of the samples at different time points during 2 hours. The samples were taken from the mouse's tail.

2. Method 2.1 Dosage

The administration dose was 10 mg/kg, and the blank was administrated with water. Both groups contained 5% DMSO.

2.2 Method of Administration

The mice were administered by gavage. 4 g/kg of 10% glucose solution was administered (0.8 mL to each mice) 15 minutes after administration.

The invention claimed is:

1. A pharmaceutically acceptable salt of (R)-7-[3-amino-4-(2,4,5-trifluorophenyl)butanoyl]-3-trifluoromethyl-5,6,7,8-tetrahydro-imidazo[1,5-a]pyrazine-1-carboxylic acid, wherein the pharmaceutically acceptable salt is a base addition salt formed between an organic or inorganic base and (R)-7-[3-amino-4-(2,4,5-trifluorophenyl)butanoyl]-3-(trifluoromethyl)-5,6,7,8-tetrahydro-imidazo[1,5-a]pyrazine-1-carboxylic acid.

2. A pharmaceutically acceptable salt of claim 1, wherein the base addition salt is selected from the group consisting of sodium, lithium, potassium, calcium, magnesium, tetramethylammonium, tetraethylammonium, ethanolamine, choline, lysine, arginine, methylammonium, dimethylammonium, trimethylammonium, triethylammonium, and ethylammonium.

3. A pharmaceutically acceptable salt of claim 1, wherein the base addition salt is ethanolamine or choline.

4. A pharmaceutically acceptable salt of claim 1, wherein the salt is selected from:

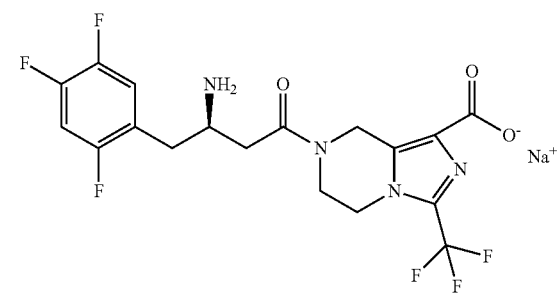
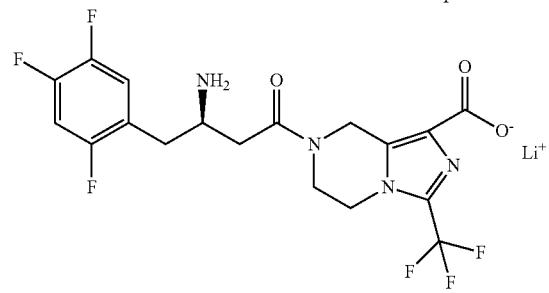
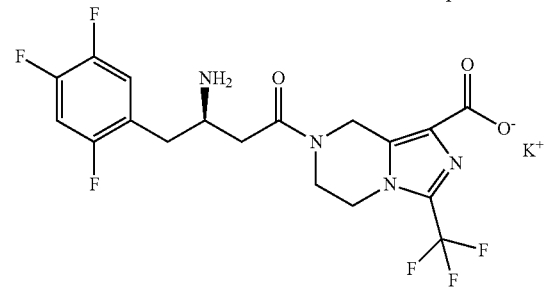
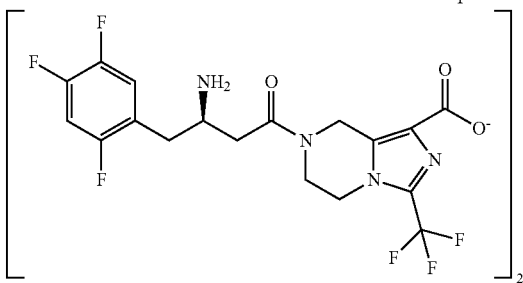
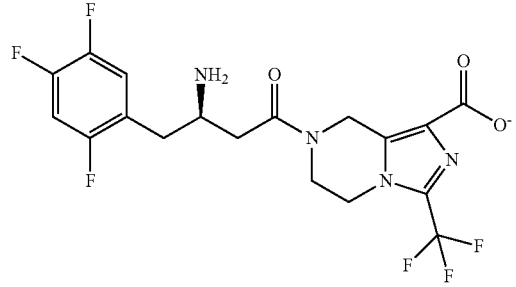
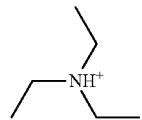
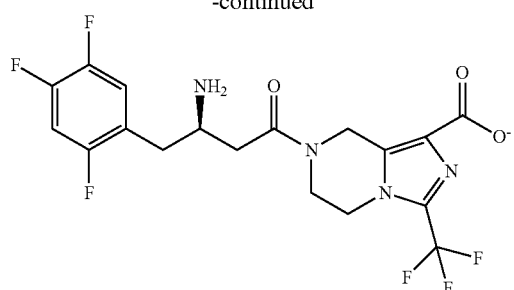
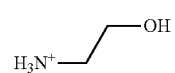
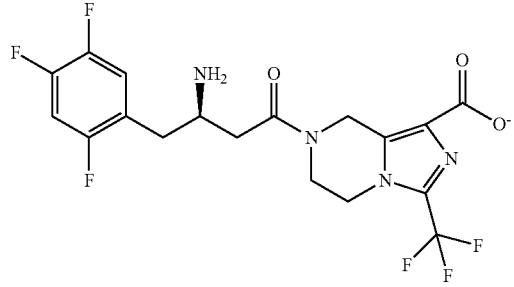
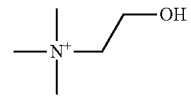
or
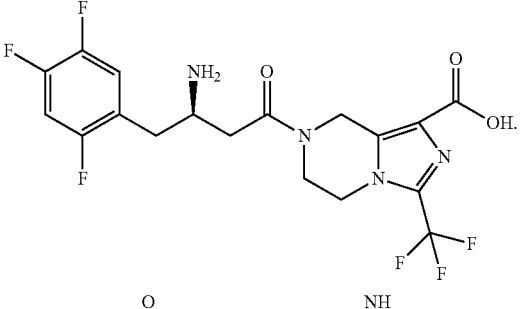
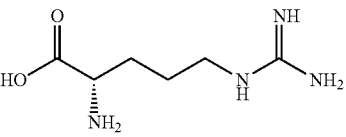
5. A pharmaceutical composition comprising therapeutically effective amount of the pharmaceutically acceptable salt of claim 1 and a pharmaceutically acceptable carrier.
* * * * *